United States Patent [19]

Keppel et al.

[11] Patent Number: 4,987,903

[45] Date of Patent: Jan. 29, 1991

[54] METHOD AND APPARATUS FOR IDENTIFYING AND ALLEVIATING SEMANTIC MEMORY DEFICIENCIES

[76] Inventors: William Keppel, 11640 SW. Boones Ferry Rd., Portland, Oreg. 97219; Kenneth R. Erickson, 21414 SW. Martinazzi Ave., Tualatin, Oreg. 97062

[21] Appl. No.: 271,164

[22] Filed: Nov. 14, 1988

[51] Int. Cl.$^5$ .............................................. A61B 5/04
[52] U.S. Cl. ..................... 128/732; 128/731
[58] Field of Search ............... 128/731, 732, 733, 745; 364/413.02

[56] References Cited

U.S. PATENT DOCUMENTS

| | | | |
|---|---|---|---|
| 4,184,485 | 1/1980 | Agoston | 128/732 |
| 4,216,781 | 8/1980 | John | 128/731 |
| 4,230,125 | 10/1980 | Schneider | 128/731 |
| 4,493,327 | 1/1985 | Bergelson et al. | 128/731 |
| 4,699,153 | 10/1987 | Shevrin et al. | 128/745 |
| 4,753,246 | 6/1988 | Freeman | 128/731 |
| 4,794,533 | 12/1988 | Cohen | 128/731 |
| 4,841,983 | 6/1989 | Duffy | 128/731 |

Primary Examiner—Lee S. Cohen
Assistant Examiner—Kennedy J. Schaetzle
Attorney, Agent, or Firm—William A. Birdwell

[57] ABSTRACT

A method and apparatus for identifying and alleviating semantic memory deficiencies. An electroencephalogram signal is detected from the scalp of a subject to produce a signal representative of evoked response potentials. The subject is instructed to perform a semantic memory task in response to a stimulus. The amplitude of the most positive-going peak of the evoked response potential signal during the 270-550 ms period following the stimulus is measured. To determine whether the subject suffers from early Alzheimer's disease, the amplitude of the signal is compared to a standard determined by applying the same method to normal subjects. The amplitude of the signal may also be used to provide a feedback signal to the subject for training the subject to improve the subject's semantic memory skills. An apparatus is provided for implementing these steps using digital signal processing, and for providing a biofeedback signal to the subject.

16 Claims, 4 Drawing Sheets

METHOD AND APPARATUS FOR IDENTIFYING AND ALLEVIATING SEMANTIC MEMORY DEFICIENCIES

BACKGROUND OF THE INVENTION

This invention relates to methods and apparatuses for identifying and alleviating deficiencies in the performance of semantic memory tasks, and particularly to the early diagnosis and treatment of Alzheimer's disease by identifying, as a symptom thereof, deficiencies in the performance of semantic memory tasks.

Studies of event-related potentials in subjects with dementia caused by Alzheimer's disease (Dementia of the Alzheimer Type, or "DAT") have demonstrated prolonged "P300" latencies in a majority of those subjects. An event-related potential ("ERP") is an electrical potential produced at the scalp of an individual representative of brain electrical activity resulting from the brain's response to external stimuli. It is picked up as a standard electroencephalograph ("EEG") signal and can be represented as a waveform of electrical potential as a function of time. The P300 component of that signal is the component with the most positive-going peak of the waveform in the latency range of 270 through 550 milliseconds. Latency means the time period following presentation of a stimulus until the subject event occurs. Ordinarily, an ERP exhibits a P300 component in response to perception by the subject of an unexpected or low-probability stimulus.

However, in the aforementioned studies, subjects from several etiologic groups were combined, and their pattern of cognitive deficits was not detailed. Thus, P300 prolongation could have been due to non-specific deficits in perceptual processing or attention capacity. Moreover, those studies used a simple auditory tone discrimination task, which was found not to be very sensitive in cases of mild dementia.

The diagnosis of Alzheimer's disease is most difficult in its early stages when only mild dementia is likely to be caused. This is because distinguishing the pathological memory loss caused by Alzheimer's disease from the far more common benign senescent forgetfulness has heretofore not been possible until the memory disorder is quite advanced, by which time the effects of associated cognitive impairments on mental status testing, coupled with a thorough evaluation, can bring the diagnostic accuracy to around 90 percent.

Early diagnosis of Alzheimer's disease is an important goal, as it can lead to better understanding of, and possible remedial strategies for, mild cognitive impairment, and can also permit more prompt treatment. A more powerful ERP technique than the classic auditory tone paradigm would therefore be helpful as a diagnostic and treatment tool.

It has previously been shown that, in young intact subjects, tasks that require processing of word meanings (semantic processing) enhance the amplitude of the P300 response associated with processing of the word meanings (as well as later memory for the word meanings) relative to tasks that only require phonologic or orthographic processing of the word. A semantic memory task will be defined herein as a task which involves the attempt to identify a stimulus as having a meaning to the subject. It would be desirable if the response to such tasks could be employed to diagnose early dementia of the type associated with Alzheimer's disease.

Electroencephalograph signals have previously been employed to ascertain the functional characteristics of a subject. For example, in John U.S. Pat. No. 4,216,781, analysis of a subject's brain wave responses to stimuli is used to determine, inter alia, the subject's ability to distinguish between symbols. Bergelson, et al. U.S. Pat. No. 4,493,327 discloses ascertaining the presence or absence of brainstem evoked potentials in response to a stimulus. Rickards, U.S. Pat. No. 4,462,411 discloses measuring evoked potentials in response to an audio stimulus to determine the subject's hearing ability. And, Silva, et al. U.S. Pat. No. 4,008,712 and Agoston U.S. Pat. No. 4,184,485 appear to disclose systems for producing an audio indication of a person's brain wave frequency for measurement and biofeedback purposes. However, none discloses the measurement of P300 amplitude as a means for identifying semantic memory task deficiencies, or treating them.

SUMMARY OF THE INVENTION

The present invention provides a means for identifying and alleviating semantic memory deficiencies. While an important application of the invention is in the diagnosis and treatment of Alzheimer's disease, it may also be used to identify and alleviate semantic memory deficiencies stemming from other causes. It may further be used to train persons to improve their semantic memory skills.

A sequence of symbols is presented to a subject. The subject is instructed to perform a semantic memory task in response to those symbols and to indicate the subject's conclusion in some manner. As the semantic memory task is being performed, the EEG signal of the subject is detected to produce a signal representative of the evoked response potential. The P300 amplitude is measured and compared to a standard established by testing normal subjects performing the same task. A P300 amplitude which is too low relative to the standard indicates a deficiency in performance of a semantic memory task.

To diagnose Alzheimer's disease, the preferred method employs as the sequence of symbols a visual display of male or female names. A set of infrequently repeated names is interspersed randomly among repetitions of a frequently repeated name. The subject is instructed to determine whether the symbol is a male name or a female name and to press a button indicating the subject's conclusion. A decrease in the amplitude of the P300 component evoked while performing this task has been found to be characteristic of Alzheimer's type dementia.

Biofeedback training is used to alleviate deficiencies in the performance of a semantic task. An electromyogram ("EMG") signal of the subject is detected and a signal, such as an audio tone or visual display, indicative of the subject's state of relaxation is presented to the subject. Provided that the subject's state of relaxation is sufficient, that is, that the electromyogram signal is sufficiently low, biofeedback training can take place. Another signal, indicative of the P300 amplitude, is presented to the subject while the subject is performing a semantic memory task in response to a sequence of symbols. Like the relaxation signal, the P300 signal may be presented by an audio tone or a visual display. The subject is instructed to feel better about a higher amplitude signal; that is, the subject is instructed to maximize the P300 amplitude.

A diagnostic and training system is provided to implement these methods. A stimulus and response processor provides a visual display of symbols to the subject by a graphics display device, receives on-off signals from push buttons operated by the subject to indicate the subject's conclusion regarding the nature of the signal, produces a synchronization signal identifying the time when each symbol is presented to the subject, and thereafter produces a response signal indicating when the subject identifies the symbol. Standard electrodes are applied to the subject's head, and an EEG signal detection device produces an electroencephalograph signal therefrom. A digitizer converts the analog electroencephalograph signal to a digital representation thereof. A digital signal processor receives the synchronization, response, and EEG signals, computes the P300 amplitude, and provides an output representative of the P300 amplitude.

For biofeedback training, the digital signal processor also receives an electromyogram signal from an EMG processor connected to the subject's forehead by standard electrodes. The output of the digital signal processor is fed to an audio tone generator for providing feedback to the subject. That output may also be fed to the stimulus and response processor to cause the graphics display device to provide visual feedback to the subject.

It is therefore the principal object of the present invention to provide novel methods and apparatuses for identifying and alleviating deficiencies in the performance of semantic memory tasks.

It is a further object of the present invention to provide novel methods and apparatuses for the early diagnosis and treatment of Alzheimer's disease by identifying, as symptoms thereof, deficiencies in the performance of semantic memory tasks.

It is a further object of the present invention to employ the amplitude of evoked response potentials in an electroencephalograph signal to identify deficiencies in the performance of semantic memory tasks.

It is yet a further object of the present invention to employ the amplitude of evoked response potentials during the performance of semantic memory tasks to train a subject to improve the subject's performance of those tasks.

The foregoing and other objectives, features, and advantages of the invention will be more readily understood upon consideration of the following detailed description of the invention, taken in conjunction with the accompanying drawings.

DESCRIPTION OF THE PREFERRED EMBODIMENT

Figure 1A:
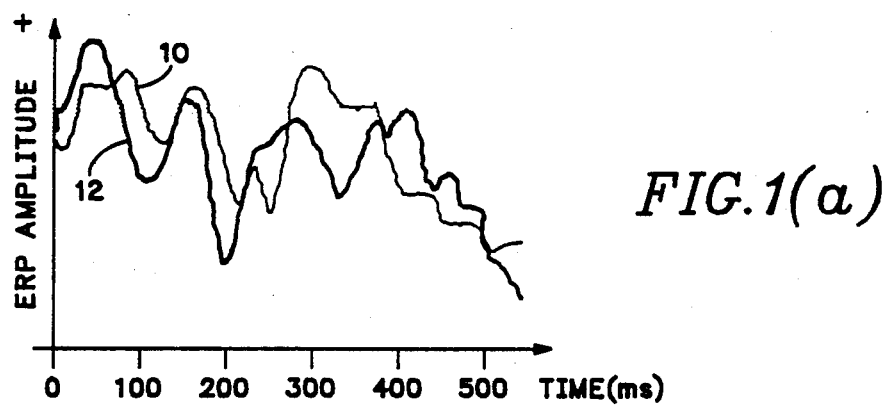
FIG. 1(a) illustrates a pair of evoked response potential waveforms produced from an EEG signal during two distinct trials of semantic memory tasks by a normal subject, each of the two waveforms representing a distinct trial.
Figure 1B:
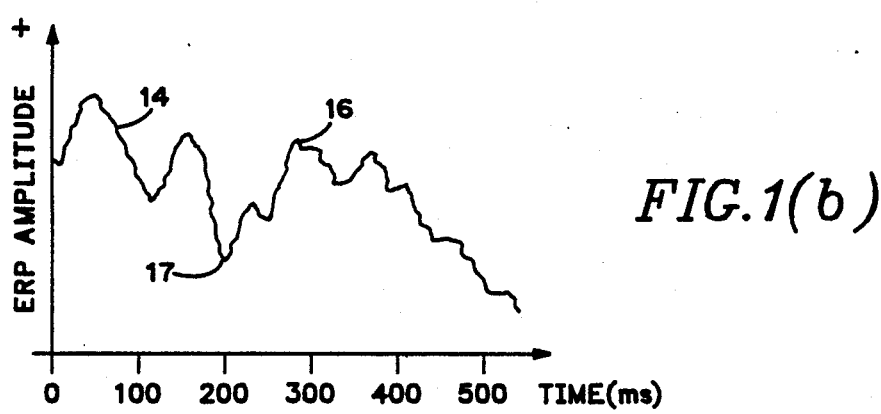
FIG. 1(b) illustrates the average of the two waveforms in FIG. 1(a).

In FIG. 1(a), two waveforms showing evoked response potentials ("ERPs") are shown. These waveforms are typically presented in units of microvolts of potential as a function of milliseconds ("ms") of time. Waveform 10 represents a first trial, that is, the ERP for a first attempt at performing a series of semantic memory tasks. Waveform 12 represents a second trial, that is, a second attempt at performing a series of semantic memory tasks. The waveform in FIG. 1(b) is L an average of the two waveforms in FIG. 1(a). To obtain this average the waveforms in FIG. 1(a) are divided into a sufficient number of time segments and the amplitudes of the waveforms for those respective time segments are averaged. As will be explained in greater detail hereafter, the present invention will preferably employ many ERP waveforms, corresponding to respective trials, which are averaged to obtain a representative ERP based upon which the subject's response to a stimulus is measured.

The waveforms shown in FIG. 1(a) are exemplary of the ERPs for a normal subject. Referring to waveform 14 in FIG. 1(b), the P300 component of the waveform, denoted by 16, is the component with the most positive peak of the ERP during the 270-550 ms latency period. As can be seen in the exemplary waveform 14, the P300 occurs at about 300 ms after the stimulus. This peak represents a response by the subject to a stimulus as a result of attempting to perform a semantic memory task.

The amplitude of the evoked response potential, and the P300 in particular, is measured in the following manner. First, a baseline amplitude is determined by averaging the ERP signal over a time period beginning 150 ms prior to the moment of stimulus and ending at the moment of stimulus. Second, the amplitude of the most negative-going peak in the 150 to 270 ms latency range is measured with respect to the baseline amplitude. That peak is known as the N200 peak and is denoted by 17 in FIG. 1(b). Third, the P300 amplitude is determined by subtracting the N200 potential relative to the baseline from the P300 potential relative to the baseline. This tends to eliminate amplitude changes not caused by responses to stimuli, such as slow shifts due to planned motor responses. While use of the baseline value is not necessary to the present invention, it is a useful technique for instances where a peak amplitude is being measured without reference to any other peak.

Figure 2A:
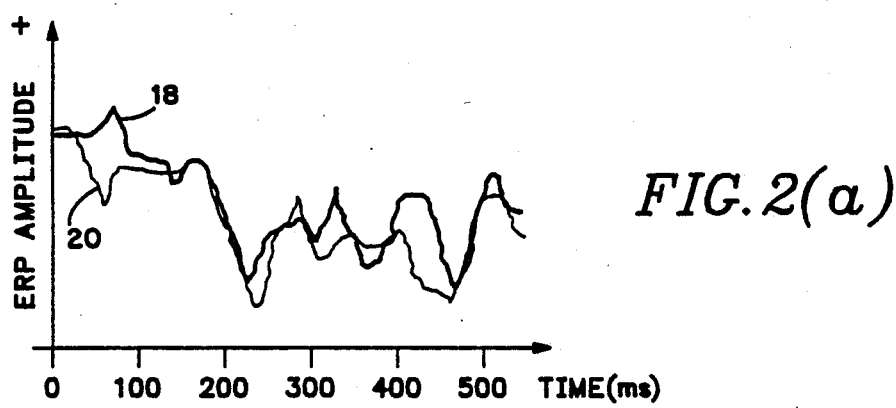
FIG. 2(a) illustrates a pair of evoked response potential waveforms produced from an EEG signal during two distinct trials of a semantic memory task by a subject having Dementia of the Alzheimer's Type, each of the two waveforms representing a distinct trial.
Figure 2B:
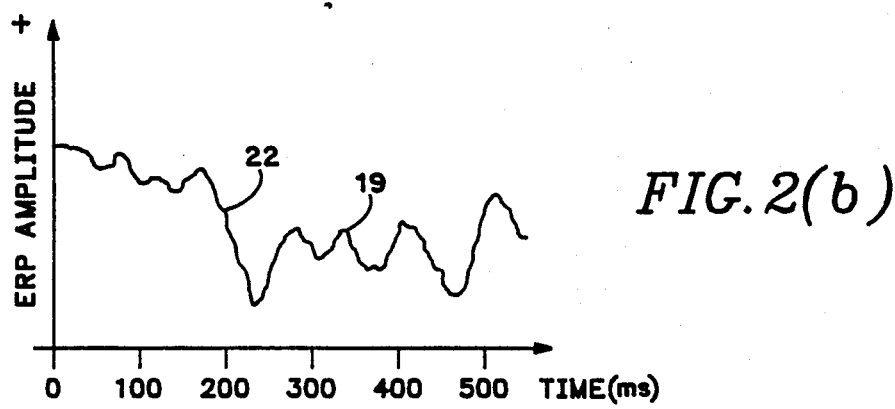
FIG. 2(b) illustrates the average of the two waveforms of FIG. 2(a).

In contrast to the waveform shown in FIG. 1(a), waveforms 18 and 20 in FIG. 2(a) represent the ERPs for two separate trials for a subject suffering from Alzheimer's disease attempting to perform the same semantic memory tasks performed by the normal subject whose ERPs are shown in FIG. 1(a). As can be seen from the average waveform 22 in FIG. 2(b), the P300 amplitude 19 for the DAT subject is greatly reduced in comparison to the P300 amplitude for a normal subject, and the P300 latency is significantly prolonged. While the P300 for the normal subject occurred at about 300 ms following the stimulus, the P300 in the DAT subject occurred at about 340 ms. Thence, by examination of the ERP waveform of a subject in light of a standard diagnostic evaluation for dementia as is commonly known in the art, it can be determined whether that subject is suffering from DAT rather than benign senescent forgetfulness.

Figure 3:
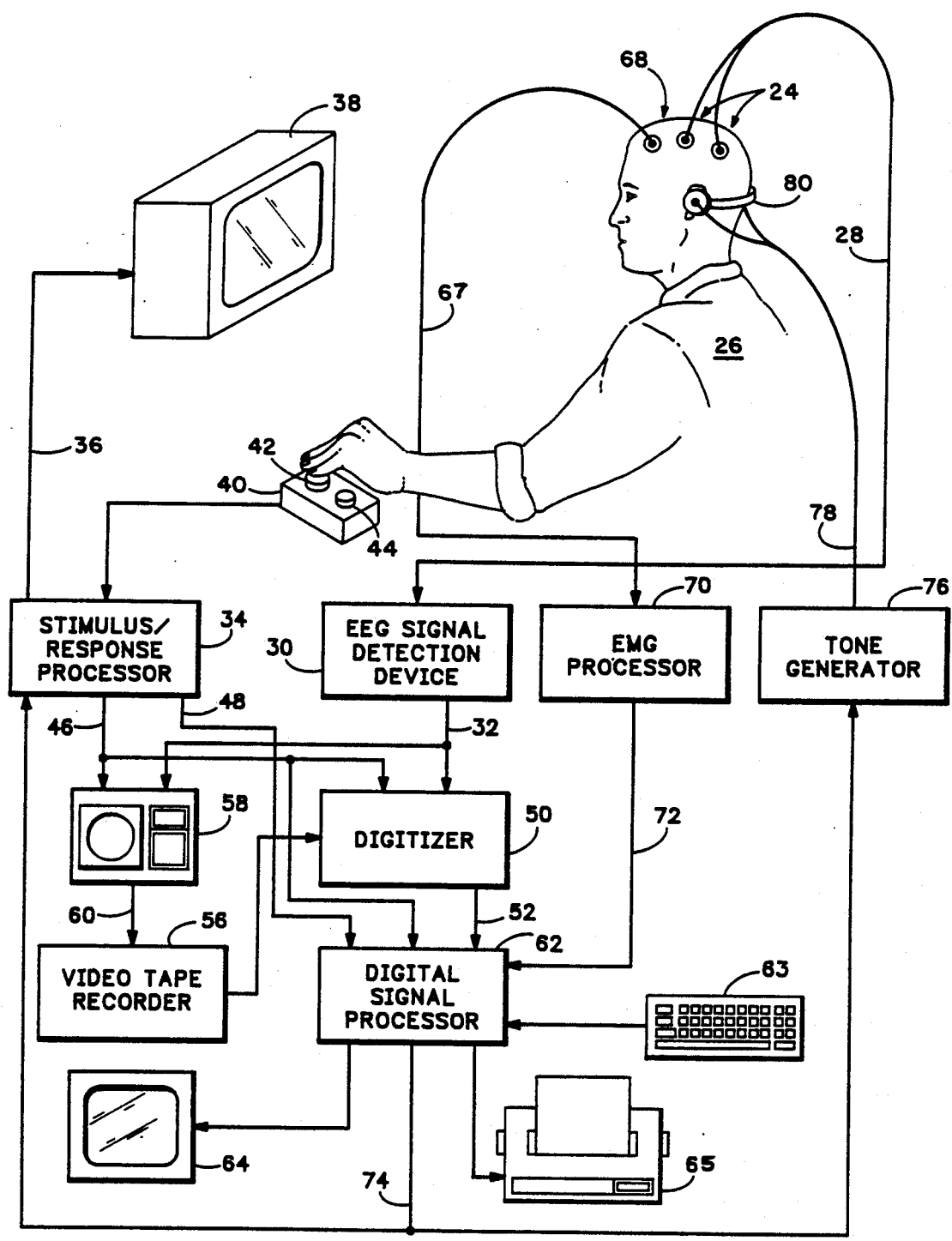
FIG. 3 is a block diagram of a system for measuring the performance of a semantic memory task and providing biofeedback in response thereto.

A system for determining the P300 amplitude and latency for the performance of a semantic memory task is shown in FIG. 3. In that system a set of electrodes 24 is attached to the head of the subject 26, in accordance with the international 10–20 electrode system, for picking up the electrical activity of the subject's brain. The electrodes 24 are connected by wires 28 to an EEG signal detection device 30 ("EEG device"). As is commonly known in the art, the EEG device produces at output 32 an electroencephalograph signal.

A stimulus and response processor 34 is provided for presenting a stimulus to the subject and receiving the subject's response. While this might be accomplished any number of ways, the stimulus and response processor is preferably a digital computer having a video output 36 connected to a video graphics display monitor 38. The computer which comprises the stimulus and response processor 34 is programmed to display a sequence of symbols on the monitor 38 for viewing by the subject 26. Preferably, as explained in more detail below, these symbols are a sequence of male and female names. The stimulus and response processor has as one input a response device 40 by which the subject 26 indicates the subject's response to the displayed symbol, that is, the stimulus. Preferably, the response device comprises a button 42 which the subject is to push if the symbol displayed is a male name, and a button 44 which the subject is to push if the symbol displayed is a female name, the buttons actually being on-off switches.

The stimulus and response processor 34 produces, as one output, a synchronization and response signal 46 which indicates the moment when the symbol was presented to the subject and the moment when the subject responded by pushing one of the buttons 42 or 44. It also provides, as another output, a type signal 48 which indicates what type of symbol was presented to the patient, for example, a frequent name or an infrequent name.

An analog-to-digital converter or "digitizer" 50 receives the synchronization and response signal 46 and the analog EEG signal 32, and converts the analog EEG signal to a digital representation, provided at output 52. While the input to the analog-to-digital converter 50 is ordinarily provided directly from the EEG device 30, it can also be provided from an EEG waveform recording device such as video tape recorder 56. In that case, the EEG signal 32 is fed to the input of an oscilloscope 58, along with the synchronization and response signal 46. The oscilloscope 58 is provided with an output 60 representing the waveform displayed on the screen of the oscilloscope. That waveform is recorded on the video tape recorder 56 along with the synchronization and type signals 46 and 48 for analysis at a later time.

The digitized EEG signal 52, the synchronization and response signal 46, and the type signal 48 are all provided as inputs to a digital signal processor 62. The digital signal processor is, preferably, a general purpose digital computer programmed to perform the analysis of the data described below, and to provide appropriate outputs. Preferably, it is equipped with an input device such as keyboard 63. A standard video display terminal 64 may be used as an output device, a printer 66 may be used as an output device, or any number of other commonly known storage or output devices may be utilized to receive the results of the data processing.

In order to provide biofeedback and training, an electromyogram signal is also picked up from the patient and analyzed to ensure that the patient is adequately relaxed to benefit from biofeedback. To that end, a set of standard EMG electrodes 68 are attached to the forehead of the patient and by wires 69 to an EMG processor 70. The EMG processor detects the electrical activity of the muscles on the forehead and produces an EMG signal 72 in a manner commonly known to the art. The EMG signal is also fed to the digital signal processor 62. A feedback output 74 of the digital signal processor, representing the P300 amplitude, is fed to a tone generator 76, which produces at output 78 an audio signal provided to the subject by a pair of headphones 80. Preferably, the frequency of the audio tone signal varies for example proportionately with increasing amplitude of the P300 signal. Similarly, the feedback signal 74 is provided as an input to the stimulus and response processor 34, which can be programmed to provide a visual indication of the P300 amplitude.

Figure 4:
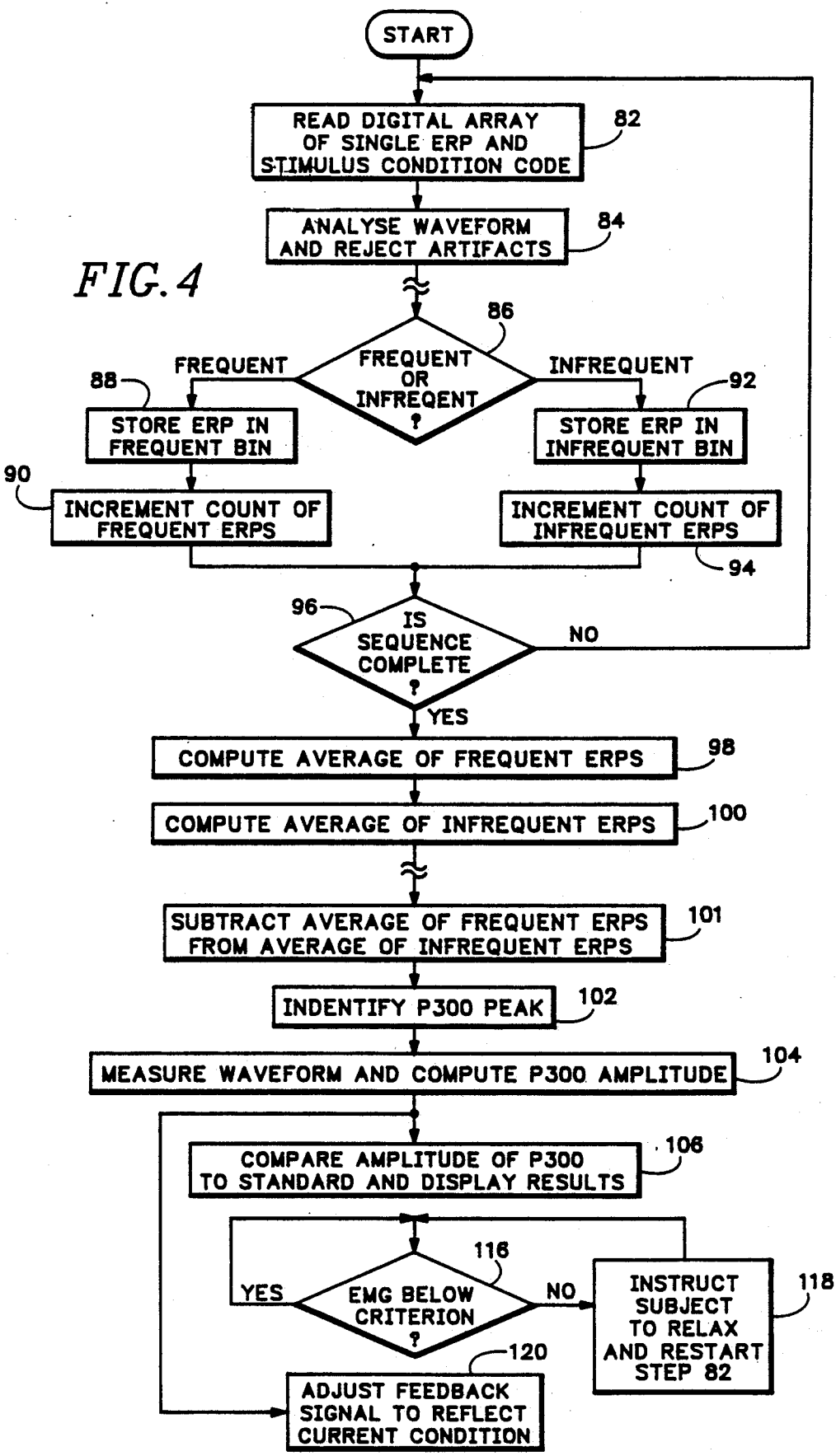
FIG. 4 is a flow chart which shows one mode of operation of the digital signal processor apparatus of FIG. 3.

Operation of the digital signal processor 62, in connection with the rest of the system shown in FIG. 3, is shown by the flow chart in FIG. 4. Preferably, the stimulus and response processor 34 presents to the subject two sequences of eighty names each. In each sequence 16 names are interspersed in pseudo-random fashion among 64 repetitions of a single name. The single name is the frequent symbol, and the 16 interspersed names are the infrequent symbols. As these names are presented to the subject, and the subject presses buttons 42 or 44 while attempting to identify the names as male or female, the digital signal processor 62 processes the event related potentials associated with each trial.

As shown in FIG. 4, in step 82 processor 62 first reads the array of digital representations of a single ERP, and reads the stimulus condition code. The processor is provided with a program for analyzing the waveform to reject artifacts which are caused, for example, by muscle jerking. Basically, this program is a low pass filter, which eliminates the high frequency components which comprise such artifacts. This is performed in step 84.

Next, in step 86, the processor 62 determines, by its input from the stimulus and response processor 34, whether the name is a frequent or infrequent name. If it was a frequent name, the digital representation of the ERP is stored, in step 88, in one storage location or "bin" for frequent names and a count of frequent names is incremented by one in step 90. Similarly, if it was an infrequent name, a digital representation of that ERP is stored, in step 92, in a bin for infrequent names, and the count of infrequent ERPs is incremented in step 94. Thereafter, in step 96, the processor tests the counts of names to determine whether the sequence is complete, and repeats the foregoing steps over and over until the sequence is complete. Once the sequence is complete, the processor 62 computes an average waveform representative of the frequent ERPs, in step 98, and an average waveform representative of the infrequent ERPs, in step 100. In step 101 the average waveform for frequent ERPs is subtracted from the average waveform for infrequent ERPs to produce a resultant waveform to be measured.

While it is possible to employ digital signal processing in step 102 to identify the N200 and P300 peaks, it has been found that in practice such identification is best done by a skilled professional. Thus, in that step, the processor 62 preferably displays the waveform on monitor 64, and the operator moves a cursor to the N200 and P300 peaks, using the keyboard 63 or another appropriate input device, to identify those peaks for the computer. For the biofeedback application, average ERPs must be rapidly computed and the P300 amplitude rapidly determined. For this purpose, the computer program identifies the P300 amplitude and provides a feedback signal reflecting the amplitude.

Once the N200 and P300 peaks are identified, they are measured and the P300 amplitude is computed by the processor 62 in step 104, as explained above. It is then compared to a standard P300 amplitude in step 106, obtained from testing normal patients, to determine whether there is a semantic memory task deficiency. The results are output, for example, to the monitor 64 or the printer 66, and for biofeedback purposes, to the video display monitor 38.

The following data illustrates the differences between subjects experiencing mild DAT and a control group.

|  | MILD DAT SUBJECTS | CONTROL (NORMAL) SUBJECTS |
| --- | --- | --- |
| Number of subjects | 6 | 6 |
| Mean age of subjects (in years) | 71.7 ± 4.3 | 69.7 ± 3.6 |
| N200-P300 difference (microvolts) | 4.57 ± 4.21 | 13.38 ± 3.42 |
| P300 latency (ms) | 424 ± 29 | 378 ± 49 |
| Mini-Mental State score (mean) | 22 | 29.5 |
| Digit span forward (mean) | 6.3 ± 0.9 | 6.7 + 0.8 |

Thus, it can be seen that for persons suffering from mild DAT, the P300 amplitude is reduced typically by an average of about 8.81 mv. It can be concluded from this data that a reduction of P300 amplitude of 6.84 mv or more indicates a high probability of DAT.

Figure 5:
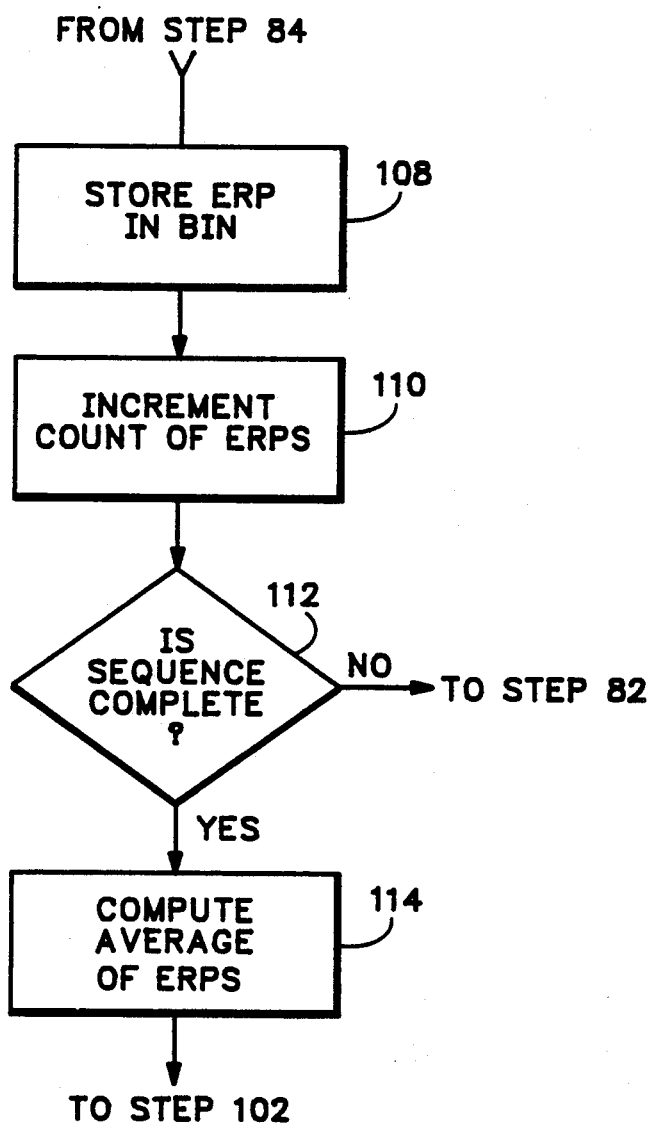
FIG. 5 is a flow chart of a modification to the flow chart of FIG. 4, which, together with FIG. 4, shows another mode of operation of the digital signal processor apparatus of FIG. 3.

FIGS. 4 and 5 show how the processor 62 provides feedback for training a subject to alleviate semantic memory task deficiencies. Preferably, the steps shown in FIG. 5 are substituted for steps 86, 88, 90, 92, 94, 96, 98, 100, and 101 of FIG. 4. That is, in accordance with an averaging technique known to persons skilled in the art, after a digital array of a single ERP is read and analyzed in steps 82 and 84 of FIG. 4, it is stored in a bin in step 108 of FIG. 5. The count of ERPs is incremented in step 110 and tested in step 112. If in step 112 the count exceeds a predetermined number of averages found sufficient to render the P300 response distinguishable from other electrical activity, then the average of the ERPs is computed in step 114. Otherwise, the process returns to step 82 of FIG. 4 and another ERP array is read However, steps 86 through 101 of FIG. 4 could be employed instead of the steps of FIG. 5 to increase the resolution of biofeedback information being provided to the subject.

While the ERPs are being processed, the EMG amplitude is continuously tested to determine whether it is below a reference level indicating that the subject is adequately relaxed, as indicated by step 116. If at any time the EMG amplitude exceeds that reference level, the subject is instructed, preferably by way of a display on the monitor 38, to try to relax more and the reading of the digital array in step 82 is restarted beginning with the next stimulus, as shown in step 118. Provided that the subject is adequately relaxed, the feedback signal is adjusted, in step 120, to reflect the current P300 amplitude, and the subject is instructed to feel positively as the P300 amplitude increases as indicated by the feedback signal provided to the subject. Semantic processing may improve as the P300 amplitude increases under these conditions.

It is to be recognized that, while the invention herein has been described in terms of performing the semantic memory task of identifying names as male or female gender names, for the purpose of diagnosing persons with mild Alzheimer's type dementia, the same measurement technique may be used for measuring the subject's performance of other types of semantic memory tasks. For example, it could be used to measure a subject's ability to recognize audio signals, such as musical chords, or to recognize tactile stimuli as well. Further, the biofeedback method and apparatus described herein may be used to train persons to improve their ability to perform a variety of semantic memory tasks, even where they are not suffering from DAT. For example, a normal subject could use the method and apparatus of this invention to improve his or her ability to remember the vocabulary of a foreign language.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A method for diagnosing Alzheimer's disease, comprising:
   (a) detecting the electroencephalogram signal from the scalp of a subject to produce a signal representative of evoked response potentials;
   (b) instructing the subject to perform a semantic memory task in response to a stimulus;
   (c) measuring the amplitude of the most positive-going peak of said evoked response potential signal during the 270-550 ms period following said stimulus; and
   (d) comparing said amplitude to a standard to determine whether said amplitude indicates an Alzheimer's disease condition.

2. The method of claim 1, wherein said semantic memory task comprises observing a visual display of a sequence of symbols, and taking some action to indicate that the subject ascribes a predetermined meaning to a given symbol, where that is so.

3. The method of claim 2, wherein said sequence of symbols comprises a set of infrequently repeated names interspersed randomly among repetitions of a frequently repeated name.

4. The method of claim 3, wherein said action comprises actuating a switch means for producing a signal representative of whether the subject ascribes a male meaning or a female meaning to an observed name.

5. The method of claim 2, further comprising presenting to said subject said visual display of a sequence of symbols, said period being measured from the time of presentation of each such symbol.

6. The method of claim 5, wherein said sequence of symbols comprises a set of infrequently repeated symbols interspersed randomly among repetitions of a frequently repeated symbol.

7. The method of claim 5, wherein said measuring step includes averaging the amplitude of said evoked response potential for each infrequently repeated symbol to produce a first average, averaging said evoked response potential for the frequently repeated symbol to produce a second average, and subtracting said second average from said first average to produce resultant data.

8. The method of claim 7, wherein said maximum positive-going peak is measured by computing the difference between the amplitude of the maximum positive-going peak of said resultant data during the 270–550 ms period following said stimulus and the amplitude of the maximum negative-going peak of said resultant data during the 150–270 ms period following said stimulus.

9. The method of claim 1, wherein said standard is the amplitude of the maximum positive peak for a set of subjects who do not have Alzheimer's disease.

10. The method of claim 1, wherein said comparing step is performed by digitizing said evoked response potential signals and analyzing the digital representation of those waveforms.

11. An apparatus for diagnosing Alzheimer's disease, comprising:
  (a) detection means for detecting the electroencephalogram signal from the scalp of a subject to produce a signal representative of evoked response potentials;
  (b) display means for displaying symbols to a subject in a predetermined manner;
  (c) input means for receiving from the subject a signal representative of whether the subject ascribes meaning to a given symbol; and
  (d) measurement means for measuring the amplitude of the most positive peak of said evoked response potential signal during the 270–550 ms period following the display of a given symbol.

12. The apparatus of claim 11, wherein said measurement means comprises digitizer means for receiving said evoked response potentials from said detection means and producing a digital representation thereof, and digital computer means for operating on said digital representation to determine said amplitude.

13. The apparatus of claim 12, wherein said display means includes means for presenting to said subject a sequence of symbols comprising a set of infrequently repeated names interspersed randomly among repetitions of a frequently repeated name.

14. The apparatus of claim 13, wherein said digital computer means is programmed to average the amplitudes of said evoked response potential for infrequently repeated symbols to produce a first average, average the amplitude of said evoked response potentials for the frequently repeated symbols to produce a second average, and subtract said second average from said first average to produce resultant data.

15. The apparatus of claim 14, wherein said digital computer means is programmed to subtract the amplitude of the maximum negative-going peak of said resultant data during the 150–270 ms period following said stimulus from the amplitude of the maximum positive-going peak of said resultant data during the 270–550 ms period following said stimulus.

16. The apparatus of claim 12, wherein said digital computer means is programmed to compare the amplitude of said most positive-going peak to a standard amplitude and provide the difference therebetween.

* * * * *